United States Patent [19]
Lindquist et al.

[11] Patent Number: 5,882,598
[45] Date of Patent: Mar. 16, 1999

[54] WAFER GAP CONDUCTIVITY CELL FOR CHARACTERIZING PROCESS VESSELS AND SEMICONDUCTOR FABRICATION PROCESSES AND METHOD OF USE

[75] Inventors: Paul George Lindquist, Eagle; Robert Newell Walters, Boise, both of Id.

[73] Assignee: SCP Global Technologies, Boise, Id.

[21] Appl. No.: 660,113

[22] Filed: Jun. 7, 1996

Related U.S. Application Data

[60] Provisional application Nos. 60/000,116 Jun. 9, 1995 and 60/014,067 Mar. 25, 1996.

[51] Int. Cl.$^6$ .................................................. G01N 27/00
[52] U.S. Cl. ........................ 422/82.02; 205/705; 205/789; 205/789.5; 422/62; 422/82.01; 436/106; 436/107; 436/108; 436/150; 134/2; 134/26; 134/902; 324/425; 324/439; 324/446; 324/449
[58] Field of Search ..................................... 205/705, 789, 205/789.5; 422/62, 82.01, 82.02; 436/150, 106, 107, 108; 134/2, 26, 902; 324/425, 439, 446, 449

[56] References Cited

U.S. PATENT DOCUMENTS

| | | | |
|---|---|---|---|
| 4,778,532 | 10/1988 | McConnell et al. | 134/10 |
| 4,872,356 | 10/1989 | Barnett et al. | 73/866.5 |
| 5,069,235 | 12/1991 | Veffer et al. | 134/113 |
| 5,647,386 | 7/1997 | Kaiser | 134/113 |

OTHER PUBLICATIONS

Tonti, A., "A SImple Model For Rinsing," pp. 41–47, Oct. 14–18, 1992, Phoenix, Arizona. Proceedings of the Second International Symposium on Cleaning Technology in Semiconductor Device Manufacturing, Proceedings vol. 95–12.

Hiratsuka, Yutaka, et al., "Equipment for Wafer Cleaning Parallel Down Flow Rinse," pp. 74–81, Oct., 1995, Chicago, Illinois. Proceedings of the Fourth International Sumposium on Cleaning Technology in Semiconductor Device Manufacturing, Proceedings vol. 95–20.

Rosato, J., et al., "Studies of Rinse Efficiencies in Wet Cleaning Tools." Paper presented at the third Internaitonal Symposium on Cleaning Technology in Semiconductor Device Manufacturing, Electrochemical Society 184th Meeting, New Orleans, LA, Oct. 1993 (13 pages).

"Valco Two Position Valve Applications," Valco Instruments Co. Inc. Catalog, Analytical Components Devices and Systems, pp. 146–148.

1.0 General Description Sheet on "The Anatel A–100 Organic Carbon Analyzer," p. 1., Anatel Corp., Boulder, Co. (1993).

"Anatel A–1000, Total Organic Carbon Monitoring For Ultrapure Water Applications," pp. 2–8, Anatel Corp., Boulder, Co. (1993).

*Primary Examiner*—Lyle A. Alexander
*Assistant Examiner*—S. Carillo
*Attorney, Agent, or Firm*—Limbach & Limbach

[57] ABSTRACT

A conductivity cell for use in determining ionic concentrations in the gap between two semiconductor substrates or wafers. The wafer gap conductivity cell is composed of two flat electrodes separated by a fixed gap. The electrodes are fabricated from wafers of the same type and dimensions used as semiconductor device substrates. All or a portion of the surfaces of the wafer electrodes are coated with a conductive material. The wafer gap conductivity cell is placed in a wafer cassette or other suitable wafer holder, whose other slots are filled with wafers which are to be cleaned or subjected to another fabrication process. The cell can be used to characterize the processes used during the fabrication of semiconductor devices and assist in investigating the effect on the processes of different process vessel designs.

21 Claims, 7 Drawing Sheets

WAFER GAP CONDUCTIVITY CELL FOR CHARACTERIZING PROCESS VESSELS AND SEMICONDUCTOR FABRICATION PROCESSES AND METHOD OF USE

REFERENCE TO RELATED APPLICATION

This patent application is a non-provisional application filed under 35 U.S.C. §111(a) claiming priority under 35 U.S.C. § 119(e) (1) based on each of provisional application Ser. No. 60/000,116, filed Jun. 9, 1995, now abandoned, and provisional application Ser. No. 60/014,067, filed Mar. 25, 1996, now abandoned.

TECHNICAL FIELD

The present invention is directed to process vessels used in the semiconductor industry during wafer cleaning and various stages of device fabrication, and more specifically, to a conductivity cell for measuring the concentrations of ionic species in the gap between two wafers arranged in a cassette which is placed in a process vessel. The conductivity cell can be used to investigate the process efficiency of different vessel designs and the impact of those designs on semiconductor device fabrication processes.

BACKGROUND OF THE INVENTION

Process vessels are tanks or other containers used in the semiconductor industry as part of the device fabrication process. Process vessels are the containers in which fabrication processes such as the etching, cleaning, stripping, and rinsing of semiconductor wafers are carried out. One type of process vessel, termed a rinse tank, is used during the cleaning of the substrates or wafers on which devices are to be fabricated. The cleaning process removes particles and contaminants acquired during manufacture of the wafers. This is necessary because the presence of contaminants or residues on a substrate can adversely affect the electrical characteristics and yield of the fabricated devices.

During a cleaning process, the substrates or wafers are typically placed in a slotted cassette (sometimes termed a "boat") which is placed in a tank (process vessel) containing a cleaning agent, typically an acid bath. The acid bath is commonly formed from a mixture of an oxidant species and an acid. After immersion in the acid bath, the cassette is transferred to a rinse tank in which the treated wafers are rinsed in ultrapure water. The rinsing step is designed to quench the wafers, so that the acid solution does not continue to act on the wafers, and to dilute and remove the chemical residues from the wafer surface.

Continual efforts are made in the semiconductor industry to improve rinse tank designs in order to reduce rinse water consumption and increase wafer throughput. This is especially important as the number of device fabrication steps and wafer size increase. These efforts generally involve making measurements to determine how quickly and completely the contaminants and oxidant solution are removed from the surface of the wafers during the rinse process. Methods currently employed to improve rinse tank and rinse process efficiency include minimizing the tank volume, reducing the wetted surface area by use of a reduced cassette, utilizing dilute chemistries, and increasing the temperature of the rinse water.

In addition, rinse tank structure designs can be optimized through the use of computational fluid dynamics, followed by experimental verification. To date, most published data used to characterize and model the rinse process within a rinse tank (or another fabrication process being carried out in a different process vessel) has been acquired by means of a wall mounted conductivity probe. While this provides useful information, there are many drawbacks to wall mounted probes: 1) The probe does not provide a direct measurement of the conductivity (and by inference, ion concentration) in the wafer gap between two wafers; 2) Probe performance is affected by changes in tank configuration and flow field; and 3) The probe response to different carry over chemistries does not correlate quantitatively to the amount of carry over on the wafer during rinsing. Because the placement of the probe on a tank wall interferes with the normal fluid flow within the rinse tank, the measurements obtained in this manner contain an inherent source of error as they are based on a disturbed tank flow and are measured at a location way from the surface of interest.

Other process vessels, such as those used to perform etching or photoresist stripping stages of the fabrication process are also candidates for investigation and design improvements. In order to improve such process vessels and the related fabrication processes, it is desirable to have a means of collecting accurate data on the impact of changes of the relevant vessel variables on the operation of different process vessel designs. This permits the identification of design changes which improve the efficiency of the processes carried out in the vessels.

What is desired is an alternative type of conductivity cell or probe which overcomes the disadvantages of wall probes currently used for characterizing the fluid flow within a process vessel and investigating the efficiency of fabrication processes conducted within the vessel.

SUMMARY OF THE INVENTION

The present invention is directed to a conductivity cell for use in determining ionic concentrations in the gap between two semiconductor substrates or wafers. A conductivity probe is used because the conductivity of a well mixed solution is proportional to the ion concentration. Thus, the measured conductivity reflects the ion concentration in the wafer gap. The wafer gap conductivity cell of the present invention is composed of two flat electrodes separated by a fixed gap. The electrodes are fabricated from wafers of the same type and dimensions used as semiconductor device substrates. All or a portion of the surfaces of the wafer electrodes are coated with a conductive material such as gold. The wafer gap conductivity cell is placed in a wafer cassette or other suitable wafer holder, whose other slots are filled with wafers which are to be cleaned or subjected to another fabrication process. The wafer gap conductivity cell can be used to characterize the wafer rinsing process and assist in investigating the effect of different rinse tank designs on the rinse process. The cell can also be used to characterize other stages of the semiconductor device fabrication process which are conducted in other types of process vessels.

Further objects and advantages of the present invention will become apparent from the following detailed description and accompanying drawings.

DETAILED DESCRIPTION OF THE INVENTION

The following detailed description focuses on application of the wafer gap conductivity cell of the present invention to the characterization of rinse tanks and wafer rinsing processes. However, it is to be understood that this is for purposes of example, and that the present invention may be used to characterize other semiconductor device fabrication processes (etching, cleaning, photoresist stripping, etc.) and to investigate the effect on such processes of possible designs of other types of process vessels.

A conductivity cell is generally composed of two electrodes between which is a region (termed the cell "gap") whose conductivity is measured. This is done by including the cell in a circuit which contains a voltage source and a device for measuring the conductivity of the cell gap region based on the current flow through the circuit.

Although there are many possible configurations for a conductivity cell, we have recognized that the ideal conductivity cell is constructed of two flat electrodes separated by a fixed gap. In addition, in order to minimize the disruption of the normal fluid flow within a rinse tank (or other process vessel) during conductivity measurements, we have recognized that it is desirable that the cell electrodes have a shape and size which corresponds as closely as possible to that of the objects normally placed in the tank. Thus, we have chosen to fabricate electrodes for a conductivity cell from a pair of wafers of the type normally used as semiconductor device substrates.

The cell is made by treating semiconductor wafers so as to form a pair of electrodes. The electrodes are then inserted into a cassette or other suitable wafer holder which is placed into the process vessel (in this example a rinse tank). Electrical connections to the electrodes permit measurement of the conductivity in the gap between the wafer electrodes using a voltage source and a current meter. Assuming the ionic concentration is proportional to the conductivity, this provides a measure of the concentration of ionic species within the gap. As a result, the effectiveness of a particular rinse tank or rinse process at removing the ionic species can be investigated. The cell can thus be used to quantify the rinsing behavior of typical wafer surfaces when the carry over chemistry is varied and is a useful tool to examine the effects of changing tank geometry and fluid flow on the efficiency of the rinse process. As noted, the present invention may also be used to investigate the efficiency of other fabrication processes and the impact of process vessel design variations on those processes.

Figure 1A:
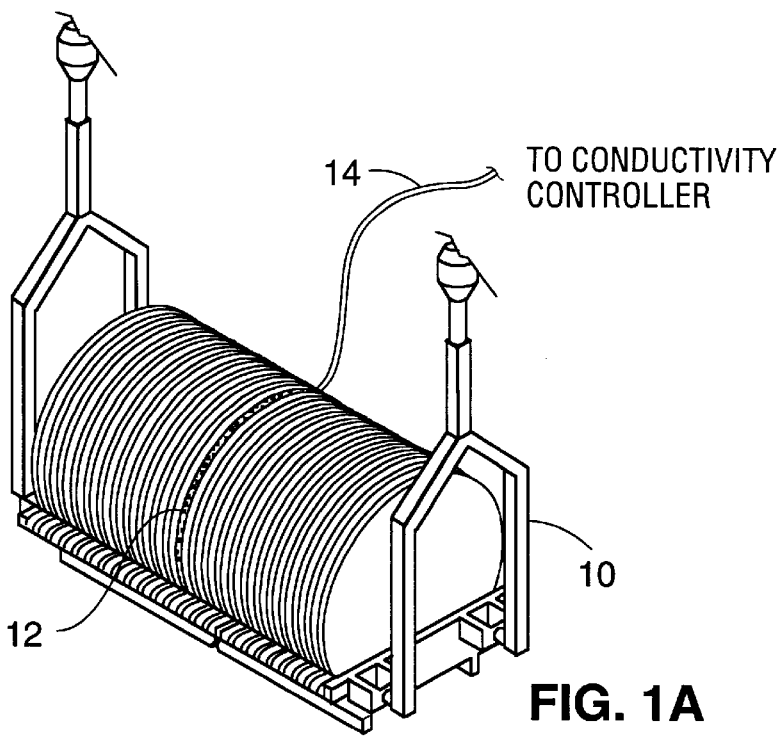
FIG. 1A shows a wafer cassette or wafer holder used for transferring wafers from a chemical tank to a rinse tank and in which the wafer gap conductivity cell of the present invention is placed.

FIG. 1A shows a wafer cassette 10 used for transferring wafers from a chemical tank to a rinse tank, and in which the wafer gap conductivity cell 12 of the present invention is placed. Another suitable type of wafer holder may also be used. Cell 12 is shown placed in cassette 10 in the position of two of the wafers normally in the cassette. Electrical leads 14 are used to connect the electrodes formed from the wafers which are part of cell 12 to other circuit elements used to measure the conductivity of the region between the electrodes. The electrical leads may be connected to the wafer gap electrodes by several methods, including solder, ultrasonic wire bonding, etc. For the experiments to be described, the leads were attached by soldering the wires to the electrodes, then coating the connection with a sealant to prevent electrical shorts.

Figure 1B:
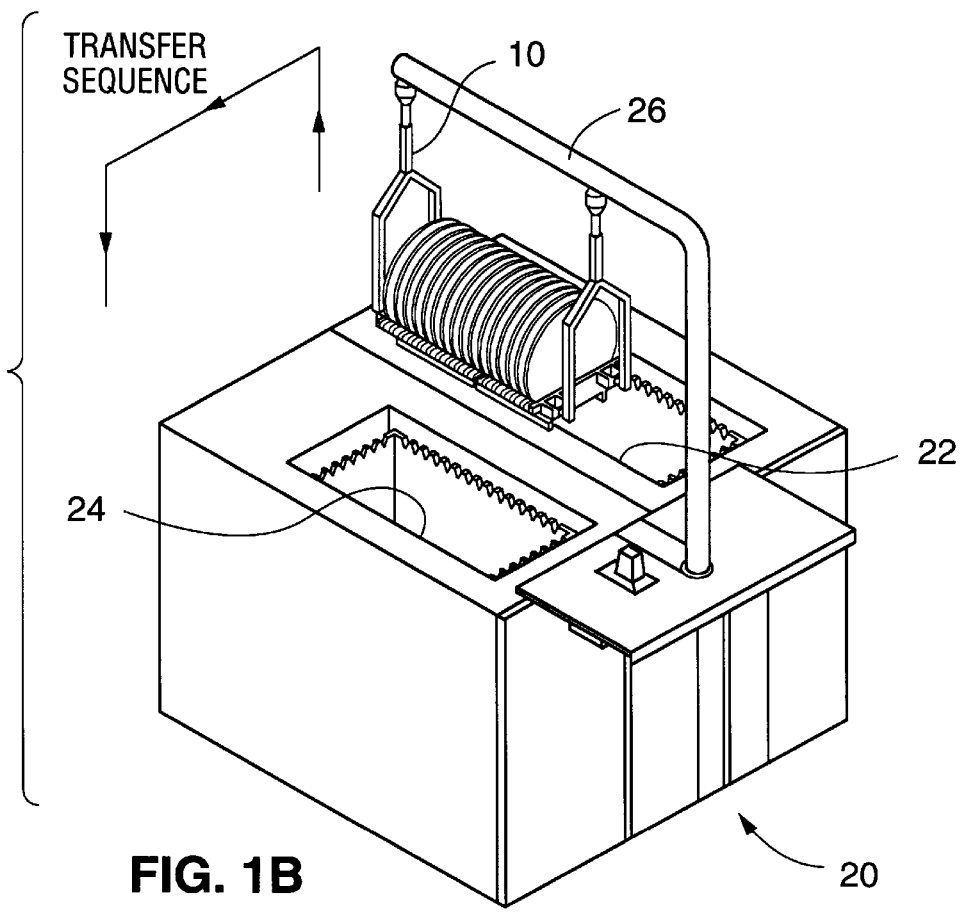
FIG. 1B shows a typical wafer transfer system for transferring a cassette of wafers between a chemical tank and a rinse tank during a cleaning process.

FIG. 1B shows a typical wafer transfer system 20 for transferring a cassette (or other wafer holder) of wafers 10 between a chemical tank 22 and a rinse tank 24. In a typical processing sequence, cassette 10 is filled with wafers and immersed in chemical tank 22 using arm 26. The wafers in cassette 10 are treated in chemical tank 22 to remove particulate matter or other contaminants as part of a cleaning process. Cassette 10 is then lifted by arm 26 and placed into rinse tank 24. Rinse tank 24 is typically filled with ultrapure water which is used to rinse the treated wafers. By replacing two of the wafers normally in cassette 10 with the wafer gap conductivity cell of the present invention, the conductivity (and by inference, the ionic concentration) in the region of the wafer gap between the two electrodes can be measured. This permits a determination of the efficiency of the rinse process and of the effects of various rinse tank designs on the rinsing process.

Electrodes for the wafer gap conductivity cell of the present invention were fabricated from two 200 mm silicon wafers of the standard shape and size used for fabrication of semiconductor devices, and which are designed to fit into the cassette or other suitable wafer holder. Each wafer is coated on one side with a 2,000 nm thick layer of chromium, followed by a 20,000 nm thick layer of gold. The conductive layers are deposited by metal evaporation in order to form the electrodes. Other conductive materials, such as platinum, titanium, doped silicon, or semiconductors may also be used to form the electrodes. Spacers fabricated from PTFE were used to keep the electrode surfaces of the conductivity cell parallel and facing each other, and to fix the electrode gap at 5.7 mm, which is the same pitch as the wafers in a typical cassette. The gap may be varied to study systems in which cassettes having a different pitch might be used.

The cell constant for this electrode configuration was calculated as 0.0018 $cm^{-1}$ and determined experimentally to be 0.0017 $cm^{-1}$. Note that although the described electrode is formed by covering the entire surface of a wafer, thereby obtaining macroscopic experimental data, microscopic data may be obtained by covering only a portion of the wafer surface area with the conductive material. Examples of such alternate electrode patterns include ring shaped electrodes, strip electrodes, and patterned electrodes.

The inventors conducted a series of experiments to determine the effectiveness of the wafer gap conductivity cell at characterizing various rinse processes and rinse tank configurations. For each rinse test, the cell replaced 2 wafers of the 50 used in a fully loaded cassette. Although the conductivity cell can be interchanged with any two wafers in the cassette, the cell was positioned in slots 25 and 26 for most of the tests. A two-channel AC conductivity meter was used to monitor the conductivity as a function of time. Channel one was used for the wafer gap conductivity cell of the present invention and channel two was used for a wall mounted conductivity probe located at the tank weir.

The apparatus used for these experiments included a wafer gap conductivity cell, a reduced cassette capable of holding fifty 200 mm wafers spaced at 6.35 mm wafer pitch, a tank to recirculate process chemicals to be rinsed, a rinse tank flow meter, and a rinse tank. The flow field in the rinse tank was varied by altering the geometry of the fluid inlets (as represented by tank configurations A, B, C, and D). Wafers were manually transferred between tanks for rinsing experiments using a sodium chloride (NaCl) chemistry. These experiments were run on wafers in the SCP Global Technologies model SPS 9400 equipment, manufactured by SCP Global Technologies, Boise Id. Rinsing experiments with sulfuric acid, HF, SC-1 (a mixture of 1 part ammonium hydroxide (30%), 1 part hydrogen peroxide (30%), and 5 parts water), and SC-2 (a mixture of 1 part hydrochloric acid (37%), 1 part hydrogen peroxide (30%), and 5 parts water) process chemistries were run at room temperature on an SPS 9400 with automated transfers between tanks.

A typical rinse experiment is carried out as follows: 1) Soak a cassette filled with dummy wafers and the conductivity cell in the test chemistry (NaCl, $H_2SO_4$, HF, SC-1, or SC-2); 2) Transfer the wafers and cassette to the rinse tank (set up in configuration A, B, C, or D); 3) Measure the conductivity as a function of time; and 4) Repeat steps 1–3 for each test parameter (test chemistry, tank configuration, and flow rate). The test matrix used for the experiments is shown in table I.

TABLE I

EXPERIMENTAL TEST MATRIX

| Experiment | System Set Up | Parameter | Setting |
|---|---|---|---|
| 1 | Fixed Rinse Tank Design | NaCl [ppm] Flow | 100, 500, 1000 Low, High |
| 2 | Fixed NaCl [1000 ppm] | Rinse Tank Flow | A, B, C, D Low, High |
| 3 | Fixed Rinse Tank | Chemistry Flow | $H_2SO_4$, HF, SC-1, SC-2 High |

The rinse process set up, a theoretical model of the rinse process, and a rinse efficiency metric which can be used to characterize the rinse process, $\tau$ (tau), will now be discussed.

The primary mass transport mechanisms that describe the rinsing of chemical residues from an array of wafers are: 1) The out diffusion from the wafer surface into the wafer gap; and 2) The convective flow from the wafer gap out of the tank. The focus of the experiments conducted by the inventors was to investigate the convective flow through the wafer gap. Analyzing the configuration and flow field of a rinse tank with wafers, the governing convection-diffusion equation in the wafer gap is:

$$\frac{\delta c}{\delta t} + v_x \frac{\delta c}{\delta x} + v_x \frac{\delta c}{\delta z} = D\left(\frac{\delta^2 c}{\delta x^2} + \frac{\delta^2 c}{\delta z^2}\right) \quad (1)$$

Little can be done to improve the diffusion of the solute into the solvent. For most chemistries used for cleaning and etching in semiconductor manufacturing, the diffusion coefficients (D) are within a factor of two when compared to each other. Thus, neglecting diffusion in both directions and convection in the transverse direction (x), the convection-diffusion equation (1) reduces to:

$$\frac{\delta c}{\delta t} + v_x \frac{\delta c}{\delta z} = 0 \quad (2)$$

The solution of this equation has the form $$c(t) = c_0 e^{t/\tau} \quad (3)$$

where c(t) is the concentration of ions in the wafer gap as a function of time, t; $c_0$ is the concentration of ions in the cell volume at t=0; and $\tau$ (tau) is a characteristic time constant for the rinsing process.

Additional parameters which characterize the rinse process can be derived from the rinse curves of wafer gap conductivity (ion concentration) versus time. These parameters include the average velocity flow through the wafer gap, dimensional quantities (k, the mass transfer coefficient), and non-dimensional quantities (the Reynolds, Peclet, and Sherwood numbers). To compute these numbers, it is necessary to first determine the flow velocity in the wafer gap. The flow through the gap is computed by integrating the time rate of change of concentration, which multiplied by the cell volume ($V_{cell}$), gives the mass average velocity through the cell. Since the fluid system is assumed to be at constant density, this is proportional to the volume average velocity through the wafer gap. The average wafer gap velocity is then calculated as follows:

$$v = \frac{1}{t_f} \sum_{i=0}^{t_f} \frac{\Delta c_i}{c_i} \frac{V_{cell}}{1d} \quad (4)$$

where $t_f$ is the time required to finish the rinsing process, $\Delta c_i$ is the difference in concentration of species (i) between two time increments, $t_i$ and $t_{(i+1)}$, l is the distance between the electrodes, and d is the wafer diameter. Combining the velocity with the other dimensional quantities, a set of non-dimensional parameters which characterize the rinse process can be derived. These parameters are shown in table III.

EXPERIMENTAL RESULTS

Figure 2:
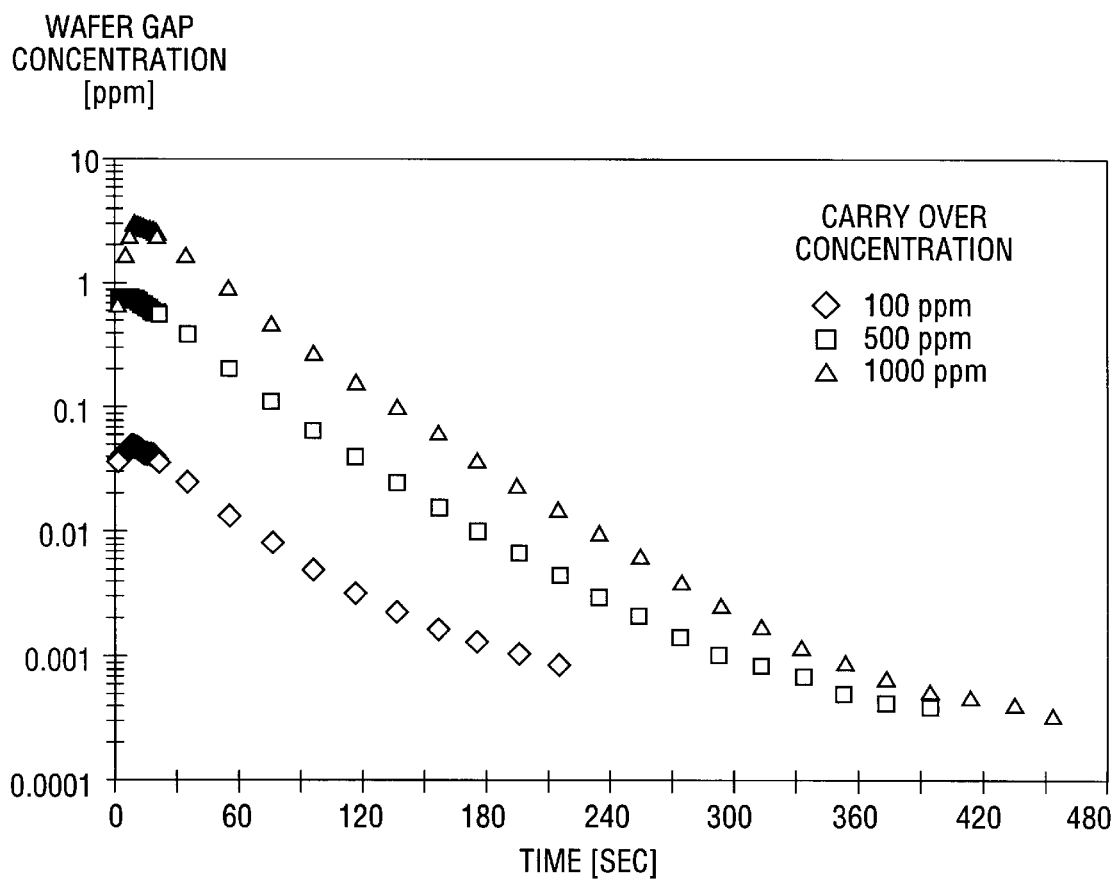
FIG. 2 is a plot of wafer gap ion concentration versus time data derived from measurements made using the wafer gap conductivity cell of the present invention for a set of NaCl rinsing experiments.

The results of experiment 1 (as identified in table 1) are shown in FIG. 2, which is a plot of wafer gap ion concentration versus time data derived from measurements made using the wafer gap conductivity cell of the present invention for a set of NaCl rinsing experiments. These results are summarized in table II. It is noted that there is a good correlation between the concentration measured by the wafer gap conductivity cell and the results predicted by equation (3). It is possible to calculate the carry over thickness, $t_{co}$, of liquid to be rinsed from the wafers using $c_0$ (from equation 3) and $c_{co}$ (the bulk concentration of the solution to be rinsed off during the experiment). Assuming that the number of ions carried over on the electrodes is equal to the number of ions measured in the cell at time (t=0), we can compute the carry over film thickness, t. The number of ions carried over is:
Number of ions=$c_{co}*V_{co}$, where $$V_{co} = (\text{carry over film thickness})*(\text{area of wafer}) = (t_{co})*(\mu d^2/4). \quad (5)$$

The number of ions in the cell at (t=0) is:

$$c_0 * V_{cell}. \quad (6)$$

Equating equations (5) and (6), and solving for t, gives an expression for the carry over film thickness:

$t = c_0 * l/c_{co}$, where $l$ is the wafer gap or distance between the electrodes.

From this analysis the carry over thickness is computed as 19 μm. These values agree with those predicted by other investigators and have been confirmed with tests run to determine the bulk carry over volume for dilute chemistries per cassette transfer for a reduced cassette.

TABLE II

Constants determined by fitting the data into equation (3) and solving for $C_0$ and τ.

| $C_{co}$ [ppm] | $C_0$ [ppm] | τ [sec] |
| --- | --- | --- |
| 100 | 0.0447 | 39.5 |
| 500 | 0.8470 | 36.0 |
| 1000 | 3.0246 | 34.7 |

Figure 3:
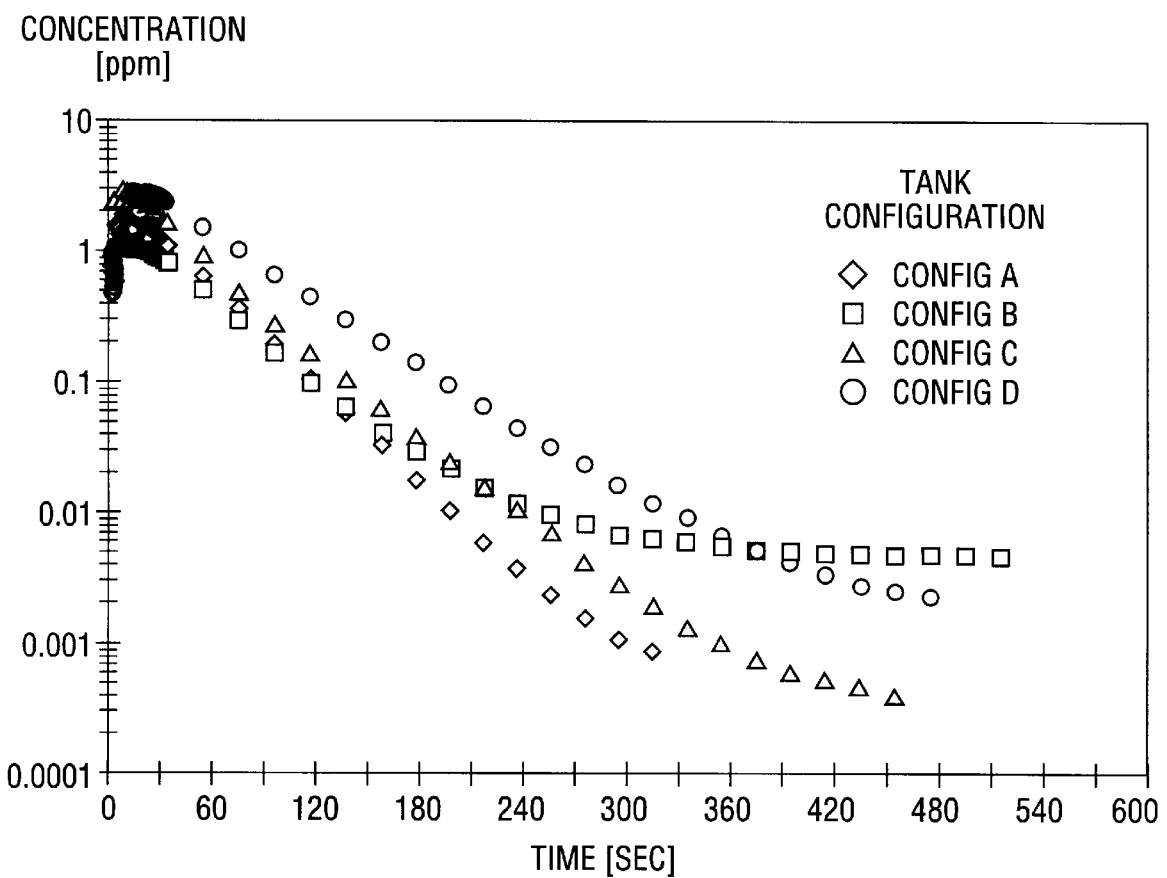
FIG. 3 is a plot of wafer gap ion concentration versus time data derived from measurements made using the wafer gap conductivity cell of the present invention for four different rinse tank configurations.

The rinsing behavior of rinse tank configurations A, B, C, and D were evaluated in a second experiment. The results are shown in FIG. 3 which is a plot of wafer gap ion concentration versus time data derived from measurements made using the wafer gap conductivity cell of the present invention for the different rinse tank configurations. Rinse parameters $c_0$, τ, the wafer gap velocity, and the Pe, Re, and Sh numbers were computed for each of the four tank configurations and are shown in Table III.

From FIG. 3 it is evident that tank D does not rinse down as fast as the other tank configurations. Using the experimentally determined τ for each configuration, it is concluded that rinse efficiency of configurations A and C are comparable. On a percentage basis, the τ for tanks A and C are 47% better than tank D. When the wafer gap velocity for tanks A and C are compared to D, there is a 29% difference between the tanks.

Figure 4:
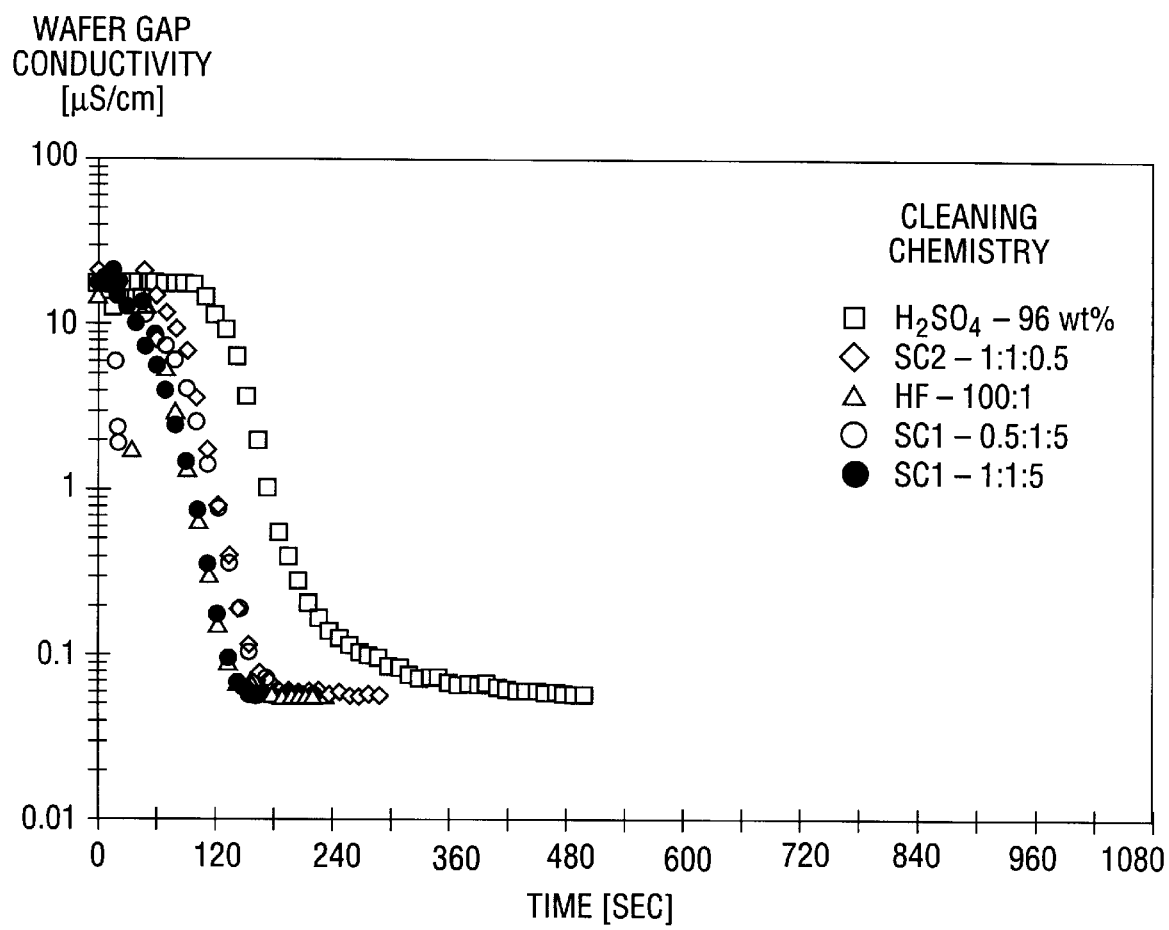
FIG. 4 is a plot of wafer gap conductivity versus time data measured using the wafer gap conductivity cell of the present invention for rinse processes following several wafer cleaning chemistries.

FIG. 4 is a plot of wafer gap conductivity versus time data measured using the wafer gap conductivity cell of the present invention for rinse processes following several wafer cleaning chemistries. Each conductivity curve is characterized by a plateau region, an exponential decay region where the concentration is modeled by equation (3), and an asymptote that approaches the conductivity of ultrapure water. The duration of the plateau region ranges from about 80 seconds for HF, SC-1, and SC-2 chemistries, to 260 seconds for sulfuric acid. We believe that the time required to transition from the plateau region to the exponential decay region is proportional to the concentration of the carry over chemistry and the thickness of the carry over layer. From this data it is apparent that the duration of the plateau region for sulfuric acid is a significant portion of the time required to carry out the rinse process. Using the wafer gap conductivity cell of the present invention, the inventors determined that the plateau duration is reduced by 100 seconds by quick dump rinsing. Rinse times can be reduced further by minimizing the quantity of sulfuric acid dragged into the tank through careful design of the robot transfer arm used to move the cassette between tanks. The time required to transition from the plateau region to the exponential decay region of the curve, or from the exponential decay region to the asymptote region depends on chemical interaction between the process chemistry and the wafer surface. For weak bases (SC-1), the transition from the plateau to the exponential decay region is not as sharp when compared to weak acids (HF) or strong acids (HCl or $H_2SO_4$). Sulfuric acid does not rise off as quickly as weak acids or bases (HF or $NH_3$) at the end of the rinse process. The important part of the curve to examine is the transition from the exponential decay to the asymptote region. Here the curve is not as sharp for sulfuric acid as compared to HF or $NH_3$.

As indicated by the preceding description, the wafer gap conductivity cell of the present invention may be used to investigate the fluid flow within a process vessel during the performance of a semiconductor device fabrication process.

TABLE III

Rinsing parameters computed for tank configurations A, B, C, and D. These parameters were computed from equations (3) and (4). For Pe, Re, and Sh: $l$ = wafer gap [cm]; D = Diffusion constant [cm$^2$/s]; V = kinematic viscosity [cm$^2$/s]; v = velocity [cm/s]; k mass transfer coefficient [cm/s].

| | Low Flow | | | | High Flow | | | |
| --- | --- | --- | --- | --- | --- | --- | --- | --- |
| Tank Configuration | A | B | C | D | A | B | C | D |
| $c_0$, ppm | 2.62 | 3.95 | 3.85 | 3.46 | 2.78 | 1.75 | 4.16 | 4.28 |
| τ, sec | 63.5 | 59.5 | 70.7 | 103.5 | 34.8 | 39.5 | 34.7 | 50.1 |
| wafer gap velocity, cm/s | 0.20 | 0.22 | 0.20 | 0.09 | 0.39 | 0.33 | 0.39 | 0.3 |
| Peclet Number, $P_e \dfrac{vl}{D}$ | 6978 | 7880 | 6981 | 3169 | 13993 | 11686 | 13785 | 10820 |
| Reynolds Number, $R_e \dfrac{vl}{V}$ | 14 | 15 | 14 | 6 | 27 | 23 | 27 | 21 |
| Sherwood Number, $S_h \dfrac{kl}{D}$ | 2211 | 2436 | 2211 | 1176 | 3857 | 3339 | 3811 | 3140 |
| k, cm/s | 0.061 | 0.068 | 0.061 | 0.032 | 0.10 | 0.09 | 0.11 | 0.09 |

This assists in investigating the impact of different process vessel designs on the effectiveness of the fabrication process, and of the relative effectiveness of the same process when carried out using different process parameters. In addition, because the present invention has only minimal impact on the fluid flow normally occurring in the process vessel, it can be used to provide a more accurate characterization of the process vessel than can be obtained using a wall mounted probe.

Another method of using the wafer gap conductivity cell is to provide a direct measurement of the convective velocity in the wafer gap. In this application, the convective velocity is determined by injecting a controlled amount of a conductive solution, such as NaCl, KCl, or a process chemical, into the bottom of the wafer gap through a capillary tube while the tank is rinsing wafers. This method has been implemented by the inventors by manually injecting a 100 $\mu$l slug of 40,000 ppm of NaCl through a 0.010" capillary tube with deionized water, as will be described with reference to FIG. 5.

Figure 5:
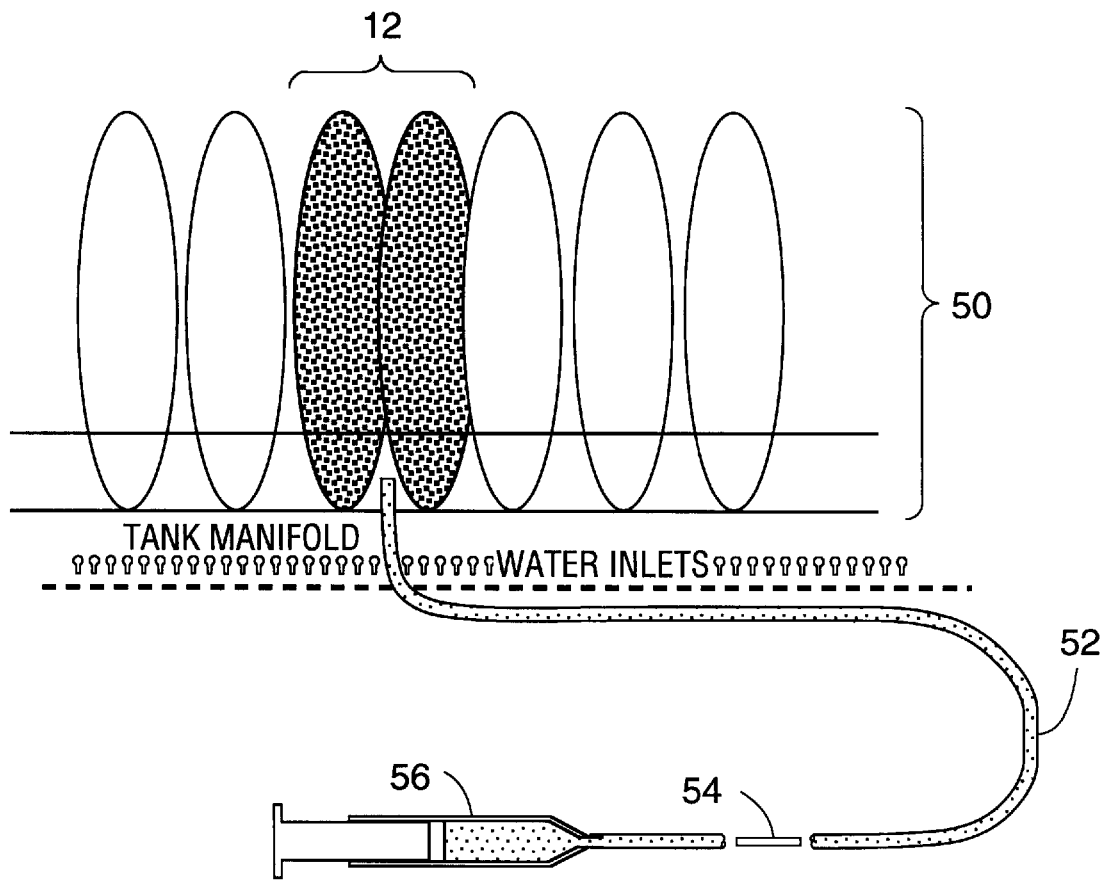
FIG. 5 is a schematic drawing showing an experimental set up in which a conductive solution is injected into the gap of the wafer gap conductivity cell in order to determine the wafer gap convective velocity.

FIG. 5 shows a schematic of wafers 50 rinsing in a tank. For this experiment, wafer gap conductivity cell 12 is placed into a cassette (or other wafer holder) and the cassette is placed in the rinse tank. A capillary tube 52 is positioned in the wafer gap, and the cell and the tank are rinsed to 0.0541 $\mu$S (18.2 MOhm). Prior to injecting a 100 $\mu$l slug of 40,000 ppm NaCl 54, the capillary is filled with deionized (DI) water. The NaCl was injected into the wafer gap with a syringe 56 filled with deionized water.

Figure 6:
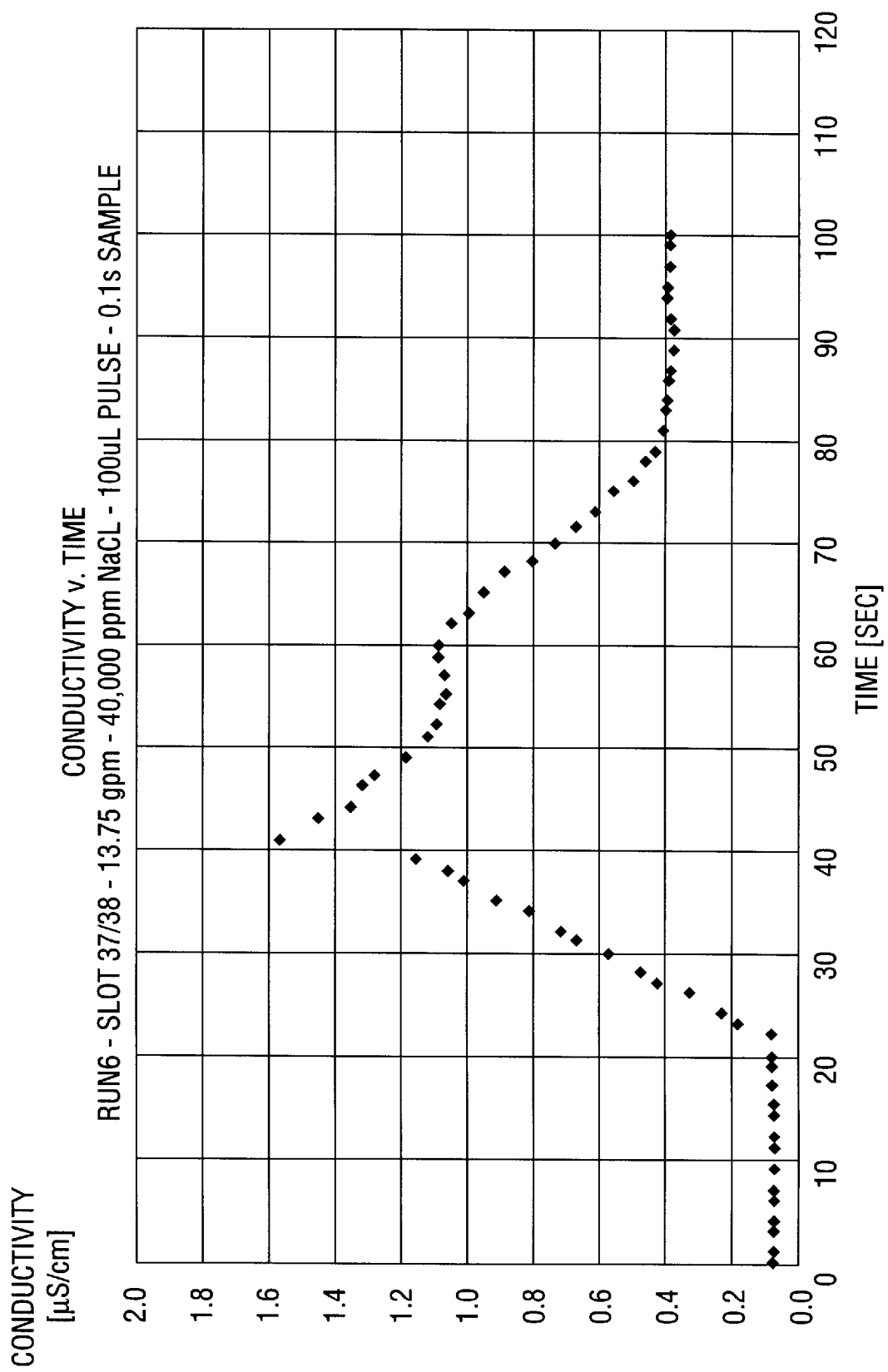
FIG. 6 is a plot of wafer gap conductivity versus time data showing the wafer gap conductivity transient caused by injecting a 100 $\mu l$ slug of 40,000 ppm NaCl solution into the wafer gap during a rinse process.

Using the experimental set up described, the conductivity in the wafer gap as a function of time was measured. The results are shown in FIG. 6. The baseline conductivity 0.054 $\mu$S/cm is shown between 0 and 20 seconds. After 20 seconds there is a steep rise in the cell conductivity, as the NaCl enters the wafer gap. At 40 seconds into the rinsing experiment the gap conductivity reaches a maximum of 1.6 $\mu$S/cm and then decreases to 1.08 $\mu$S/cm at 52 seconds. The region between 52 and 60 seconds in the rinse curve is regarded as the plateau region. After 60 seconds there is a sharp decrease in the gap conductivity, as the NaCl slug is swept from the wafer gap region of the conductivity cell. For times longer than 80 seconds, changes in wafer gap conductivity are caused by NaCl ions that recirculate in the tank.

Using the micro-injection technique described, in conjunction with the wafer gap conductivity cell, it is possible to compute the velocity of the flow inside the wafer gap. The velocity in the wafer gap is the distance the micro-injected slug travels, from the capillary to the top of the wafer, divided by the time interval of the pulse (the conductivity increase followed by decrease to a stable level) measured by the conductivity instrument.

Yet another method of using the wafer gap conductivity cell is in quantifying the amount of residue remaining in the diffusive layer at or near the wafer surface during a fabrication process. In the case of a rinse process, this gives an indication of the effectiveness of the rinse process and the rinse tank design at removing contaminants from the chemically treated wafer.

This method of characterizing a process vessel uses ultraviolet (UV) radiation to determine the amount of residue remaining in the wafer gap, or the diffuse residues on or near the wafer surface. The method uses a modified wafer gap conductivity cell, a UV light source, and a solution containing an oxidizable carbon compound, such as sucrose, as the challenge solution to be rinsed off the wafer.

Figure 7:
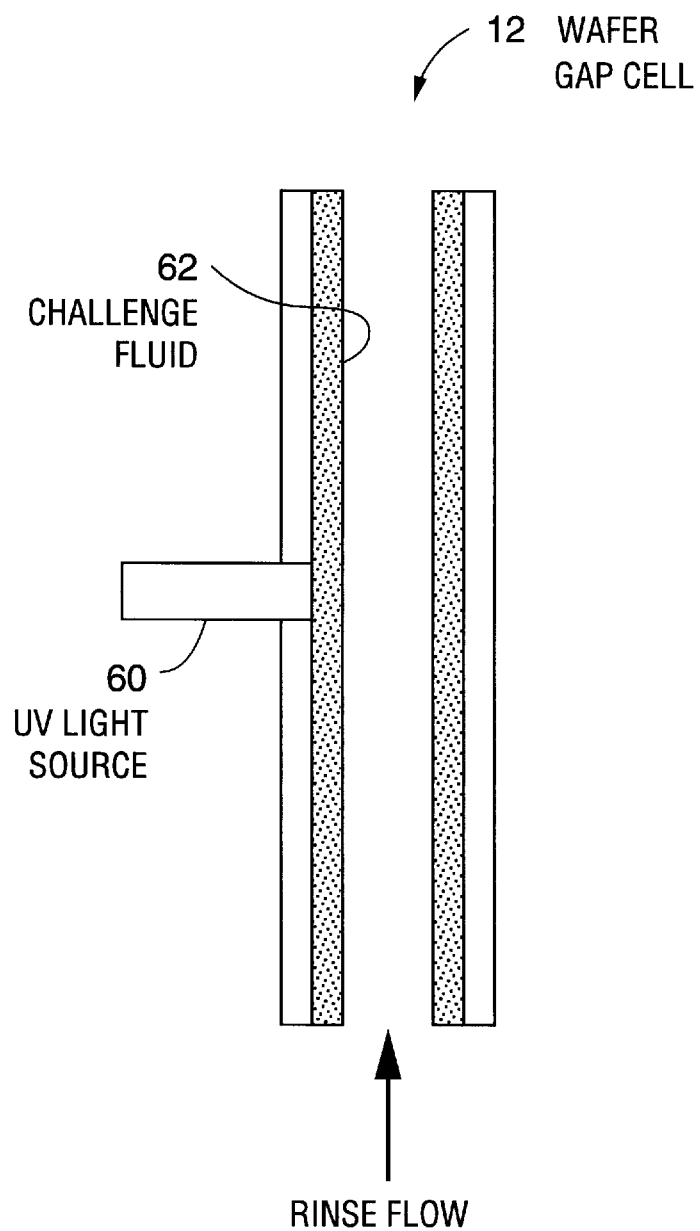
FIG. 7 shows how the wafer gap conductivity cell of the present invention may be used in conjunction with an ultraviolet light source to study the residues remaining on wafers during a rinse process.

In this experimental set up, a diffuse layer of sucrose or oxidizable carbon is oxidized by a UV light source that illuminates the wafer gap surface through a window in the wafer gap conductivity cell. FIG. 7 shows how the wafer gap conductivity cell of the present invention 12 may be used in conjunction with an ultraviolet light source 60 to study the residues remaining on wafers during a rinse process.

As shown in the figure, the electrode surfaces of wafer gap conductivity cell 12 are coated with an organic film, termed a "challenge fluid" 62 in the figure. An ultraviolet light source is oriented to illuminate the wafer gap through a window in one of the electrodes. When the organic film is exposed to the radiation, it breaks down into smaller carbon molecules and carbon dioxide. The carbon dioxide hydrates with water in the wafer gap cell and forms carbonic acid. Since carbonic acid is ionic, the change in conductivity of the solution measured by the wafer gap conductivity cell is proportional to the amount of material oxidized by the radiation. For semiconductor rinsing and process applications, this method of evaluating the efficiency of a rinse process is promising because the conductivity of ultra pure water changes many orders of magnitude when exposed to minute quantities of carbon dioxide.

This method of characterizing a rinse process or rinse tank design is useful because:

1. Other methods use ionic solutions or inorganic acids as the conductive media the wafer gap conductivity cell measures. This method uses organics that may or may not be ionic before oxidation;

2. This method is sensitive to parts per trillion concentrations of oxidizable organics;

3. The light source can be pulsed on and off to measure the residues remaining in the rinsing process;

4. There are no direct methods of currently measuring surface organics while rinsing. All methods are indirect or destructive;

5. A UV wafer gap conductivity cell is inexpensive to implement; and

6. This method extends the usefulness of the wafer gap conductivity cell for rinsing and processing applications.

The results of the described experiments indicate that the wafer gap conductivity cell of the present invention is an effective tool for evaluating process vessel designs, fabrication processes, and to determine performance parameters for the fabrication processes. A wafer gap cell is useful because mass transport in the wafer gap can be modeled from first principles, the conductivity cell replaces wafers in a cassette used for batch processing, the output from the conductivity cell can be converted to ionic concentrations in the cell volume, and the conductivity cell can be used to study rinsing of model solutions like NaCl (an ionic electrolyte) and chemistries in wafer cleaning processes.

As noted, although the use of the present invention has been described in the context of characterizing rinse tanks and rinse processes, it may also be used to investigate other fabrication processes and the design of other types of process vessels. For example, the wafer gap conductivity cell can be used to study a photoresist stripping process by coating the electrodes with photoresist and exposing them to a stripping chemistry. The electrodes will not become conductive until the photoresist is etched away, thereby providing a method of studying the progression and efficiency of the stripping process. Similarly, the present invention can be used to investigate alternative photoresist stripping tank designs, or the fluid flow in another process vessel such as a chemical etch tank. The size and shape of the conductive layer deposited on the wafers may also be varied to assist in characterizing the process tank design.

The terms and expressions which have been employed herein are used as terms of description and not of limitation, and there is no intention in the use of such terms and expressions of excluding equivalents of the features shown and described, or portions thereof, it being recognized that various modifications are possible within the scope of the invention claimed.

We claim:

1. A conductivity cell for determining a concentration of an ion species, comprising:

a first and a second cell electrode formed from a first and second semiconductor wafer of the size and shape used as a substrate for the formation of semiconductor devices, the semiconductor wafers having a front and a back surface, wherein at least a portion of the front surface of each wafer is coated with a conducting material to form the cell electrodes, and further, wherein the first and second cell electrodes are oriented in a parallel fashion with their respective front surfaces facing each other and separated by a fixed gap; and means for electrically connecting the coated portions of the front surfaces of the first and second electrodes to a circuit for determining the conductivity within the fixed gap.

2. The conductivity cell of claim 1, wherein the conducting material is selected from the group consisting of: chromium, gold, platinum, titanium, and doped silicon.

3. The conductivity cell of claim 1, wherein the front surfaces of the semiconductor wafers are fully coated with the conducting material.

4. A device for use in characterizing the efficiency of a semiconductor fabrication process or a process vessel design, comprising:

a wafer holder for holding semiconductor wafers used as substrates for the formation of semiconductor devices, the holder including a plurality of positions into which a wafer may be inserted; and a wafer gap conductivity cell for determining a concentration of an ion species, the conductivity cell being placed in the wafer holder in positions normally occupied by two semiconductor wafers, the cell further comprising a first and a second cell electrode formed from a first and second semiconductor wafer of the size and shape normally placed in the wafer holder, the semiconductor wafers having a front and a back surface, wherein at lest a portion of the front surface of each wafer is coated with a conducting material to form the cell electrodes, and further, wherein the first and second cell electrodes are oriented in a parallel fashion with their respective front surfaces facing each other and separated by a fixed gap; and means for electrically connecting the coated portions of the front surfaces of the first and second electrodes to a circuit for determining the conductivity within the fixed gap.

5. The device of claim 4, wherein the conducting material is selected from the group consisting of: chromium, gold, platinum, titanium, and doped silicon.

6. The device of claim 4, wherein the front surfaces of the semiconductor wafers are fully coated with the conducting material.

7. The device of claim 4, further comprising:

a plurality of wafers inserted into the wafer holder in the positions not occupied by the conductivity cell.

8. A method of determining the concentration of an ionic species within a process vessel used during fabrication of semiconductor devices, comprising:

preparing a wafer gap conductivity cell formed from a first and a second cell electrode, the electrodes oriented in a parallel fashion and separated by a fixed gap and being formed from a first and second semiconductor wafer of the size and shape used for the fabrication of the semiconductor devices, wherein the semiconductor wafers have a front and a back surface and the front surfaces are facing each other, and at least a portion of the front surfaces are coated with a conducting material to form the first and second cell electrodes;

inserting the conductivity cell into a wafer holder used for holding said semiconductor wafers, the holder including a plurality of positions into which a wafer may be inserted;

inserting a plurality of wafers into the wafer holder in the positions not occupied by the conductivity cell;

immersing the wafer holder in a solution within a process vessel, said solution containing an ionic species; and measuring the conductivity of a region within the gap between the two cell electrodes, the conductivity of the region being representative of the concentration of said ionic species within the gap.

9. The method of claim 8, wherein the step of preparing the wafer gap conductivity cell further comprises:

providing a means for electrically connecting the coated portions of the front surfaces of the first and second electrodes to a circuit for determining the conductivity within the fixed gap.

10. The method of claim 8, further comprising the step of:

calculating the concentration of said ionic species from said conductivity.

11. A method of determining the convective velocity of a fluid within a wafer gap between two wafers, comprising:

preparing a wafer gap conductivity cell formed from a first and a second cell electrode, the electrodes oriented in a parallel fashion and separated by a fixed gap and being formed from a first and second semiconductor wafer of the size and shape used for fabrication of a semiconductor device, wherein the semiconductor wafers have a front and a back surface and the front surfaces are facing each other, and at least a portion of the front surfaces are coated with a conducting material to form the first and second cell electrodes;

inserting the conductivity cell into a wafer holder used for holding said semiconductor wafers, the holder including a plurality of positions into which a wafer may be inserted;

immersing the wafer holder into a process vessel;

injecting a conductive solution into the fixed gap between the cell electrodes;

measuring the conductivity in the gap as a function of time; and determining the convective velocity in the gap from the measured conductivity.

12. The method of claim 11, wherein the step of determining the convective velocity in the gap from the measured conductivity further comprises:

determining the distance the conductive solution travels during a defined time interval; and dividing the determined distance by the defined time interval.

13. The method of claim 11, wherein the step of preparing the wafer gap conductivity cell further comprises:

providing a means for electrically connecting the coated portions of the front surfaces of the first and second electrodes to a circuit for determining the conductivity between the fixed gap.

14. A method for determining an amount of an oxidizable material remaining in a fixed gap between a first and a second semiconductor wafer during a semiconductor device fabrication process, comprising:

preparing a wafer gap conductivity cell formed from a first and a second cell electrode, the electrodes oriented in a parallel fashion and separated by the fixed gap and being formed from said first and second semiconductor wafers, the first and second semiconductor wafers being of a size and shape used for fabrication of the semiconductor device, wherein the semiconductor wafers have a front and a back surface and the front surfaces are facing each other, and at least a portion of the front surfaces are coated with a conducting material to form the first and second cell electrodes, and further, wherein the first electrode includes a window through with a beam of light may be projected onto the front surface of the second electrode;

coating the portions of the front surface of the second wafer which are coated with the conducting material with a layer of oxidizable material which may be oxidized by the beam of light;

inserting the conductivity cell into a wafer holder used for holding said semiconductor wafers, the holder including a plurality of positions into which a wafer may be inserted;

immersing the wafer holder into a process vessel;

projecting the beam of light through the window onto the front surface of the second electrode, thereby oxidizing the oxidizable material; and measuring the conductivity in the fixed gap as a function of time, the conductivity being representative of the amount of oxidizable material in the fixed gap between said first and second semiconductor wafers.

15. The method of claim 14, wherein the step of preparing the wafer gap conductivity cell further comprises:

providing a means for electrically connecting the coated portions of the front surfaces of the first and second electrodes to a circuit for determining the conductivity within the fixed gap.

16. The method of claim 15, wherein the oxidizable material is an organic film and the beam of light is provided by an ultraviolet light source.

17. The method of claim 16, wherein the organic film contains an oxidizable carbon compound.

18. The method of claim 17, wherein the oxidizable carbon compound is sucrose.

19. A method for studying the efficiency of a fabrication process used to remove a layer of material during the fabrication of a semiconductor device, comprising:

preparing a wafer gap conductivity cell formed from a first and a second cell electrode, the electrodes oriented in a parallel fashion and separated by a fixed gap and being formed from a first and second semiconductor wafer of the size and shape used for fabrication of the semiconductor device, wherein the semiconductor wafers have a front and a back surface and the front surfaces are facing each other, and at least a portion of the front surfaces are coated with a conducting material to form the first and second cell electrodes;

coating the front surfaces of the first and second electrodes with a layer of material to be removed;

inserting the conductivity cell into a wafer holder used for holding such semiconductor wafers, the holder including a plurality of positions into which a wafer may be inserted;

immersing the wafer holder into a process vessel which contains a chemical solution used to remove said layer;

measuring the conductivity within the fixed gap as a function of time, wherein the conductivity is representative of an amount of said layer of material removed; and determining the efficiency of the fabrication process from said measure conductivity.

20. The method of claim 19, wherein the step of preparing the wafer gap conductivity cell further comprises:

providing a means for electrically connecting the portions of the front surfaces of the first and second electrodes which are coated with a conducting material to a circuit for determining the conductivity within the fixed gap.

21. The method of claim 20, wherein the layer of material to be removed is photoresist.

* * * * *